United States Patent [19]

Kester et al.

[11] Patent Number: 4,999,430
[45] Date of Patent: Mar. 12, 1991

[54] DERIVATIVES OF 1,2,3,4-TETRAHYDRO-9-ACRISINAMINE

[75] Inventors: Jeffrey A. Kester; Walter H. Moos; Anthony J. Thomas, all of Ann Arbor, Mich.

[73] Assignee: Warner-Lambert Company, Morris Plains, N.J.

[21] Appl. No.: 387,722

[22] Filed: Jul. 31, 1989

[51] Int. Cl.$^5$ .................... C07D 219/10; A01N 43/42
[52] U.S. Cl. ...................................... 546/105; 514/879
[58] Field of Search ........................ 514/297, 298, 879

[56] References Cited

PUBLICATIONS

Stewart, J., J. Pharm. Sci., 1973, 62(8), to 1357-8.
Stewart et al., J. Med. Chem, 1970, 13(4), 762.

Chemical Abstracts, p. 80, 110:128660x.

Primary Examiner—Mukund J. Shah
Assistant Examiner—Deborah D. Carr
Attorney, Agent, or Firm—Francis J. Tinney

[57] ABSTRACT

Novel prodrugs or depot derivatives of 1,2,3,4-tetrahydro-9-acridinamine are described, as well as methods for the preparation and pharmaceutical compositions of same, which are useful as analgesic agents for the treatment of pain, as sleep aids and as agents for treating the symptoms of senile dementia, Alzheimer's disease, Huntington's chorea, tardive dyskinesia, hyperkinesia, mania, or similar conditions of cerebral insufficiency characterized by decreased cerebral acetylcholine production or release.

12 Claims, No Drawings

DERIVATIVES OF 1,2,3,4-TETRAHYDRO-9-ACRISINAMINE

BACKGROUND OF THE INVENTION

The present invention relates to novel derivatives of 1,2,3,4-tetrahydro-9-acridinamine useful as pharmaceutical agents, to methods for their production, to pharmaceutical compositions which include these compounds and a pharmaceutically acceptable carrier, and to pharmaceutical methods of treatment. More particularly, the novel compounds of the present invention are derivatives of 1,2,3,4-tetra -hydro-9-acridinamine which are useful in treating the symptoms of cognitive decline in an elderly patient.

Disorders of cognition are generally characterized by symptoms of forgetfulness, confusion, memory loss, attentional deficits and/or, in some cases, affective disturbances. These symptoms may arise as a result of the general aging process and/or from organic brain disease, cerebrovascular disease, head injury or developmental or genetic defects.

The general decrease in cognitive function which accompanies the aging process is well accepted. The same phenomenon has been observed and documented in many lower mammals, including those routinely employed in pharmacological testing programs for screening and predicting usefulness for particular drugs in higher animals, including humans.

Although disorders of cognition often accompany the general aging process, presenile and senile primary degenerative dementia are the most common accepted causes of mental deterioration in the elderly. It has been estimated that at least ten percent of persons over sixty years of age will eventually suffer severe mental deterioration. A much larger number will experience cognitive decline of sufficient severity to impede their activities.

Many of the symptoms of cognitive disorders, especially impaired memory, are associated with decreased acetylcholine synthesis and the impairment of cholinoreceptive neurons. In the hippocampus and cerebral cortex of patients suffering from primary degenerative dementia for example, the level of the enzyme choline acetyltransferase (CAT) can be reduced as much as ninety percent (see Davies, P., et al, *The Lancet*, 2, page 1403 (1976); Perry, E. K., et al, *Journal of Neurological Sciences*, 34, pages 247 to 265 (1977): and White, P., et al, *The Lancet*, 1, pages 668 to 670 (1977)).

Since CAT catalyzes the synthesis of acetylcholine from its precursors choline and acetyl coenzyme A, the loss of CAT reflects the loss of cholinergic or acetylcholine-releasing nerve endings in the hippocampus and cerebral cortex. There is abundant evidence that cholinergic terminals in the hippocampus are critically important for memory formation.

The cholinergic hypothesis suggests that drugs which restore acetylcholine levels or cholinergic function (i.e., cholinomimetic) are effective in correcting this deficit in neurotransmitter chemical and provide treatment of the memory impairment symptom of cerebral insufficiency. Considerable biochemical, pharmacological, and electrophysiological evidence supports the hypothesis that deficits in the cholinergic system underlie geriatric cognitive dysfunction (Peterson, C. and Gibson, G. E., *Neurobiology of Aging*, 4, pages 25 to 30 (1983)). Aged humans and nonhuman primates with decreased cognition show improved memory when they are treated, for example, with acetylcholinesterase inhibitors such as 1,2,3,4-tetrahydro-9-acridinamine and physostigmine. These agents increase the available supply of synaptic acetylcholine by inhibiting its hydrolysis.

1,2,3,4-Tetrahydro-9-acridinamine (tacrine; THA) has been shown to be useful in the long-term palliative treatment of patients with Alzheimer's disease (Summers, W. K., et al, *The New England Journal of Medicine*, 315, pages 1241 to 1245 (1986)). The results indicated that when the dose of tacrine was increased up to 200 mg per day the clinical response improved dramatically. However, toxic side effects also were noted when large doses of tacrine were used. Thus, there is a need to administer a therapeutically effective amount of tacrine over a prolonged period of time to a patient without the concomitant undesirable toxic side effects.

Ideally, if a drug is delivered to the target area in a controlled amount, therapy should be maximized and toxic side effects minimized.

One method of controlling the release of a drug is to derivatize as a prodrug or to localize the drug in some biological depot or site within the organism with subsequent slow release of the drug in a therapeutically effective quantity over an extended period of time. Various biologically active agents have been modified chemically to form prodrugs or depot derivatives. The derivative is then administered to a patient, localized in a biological depot and subsequently biotransformed in vivo into the active agent over an extended period of time.

A prodrug or a depot derivative has several advantages, one of which is that the patient is exposed to less total active drug in any given period of time which minimizes or eliminates local or systemic side effects. Additionally, there is a decrease in the frequency with which the patient has to take the drug. This is particularly important in the case of a patient suffering from Alzheimer's disease where patient compliance is a problem. However, the chemically altered prodrug or depot derivative may result in a drug with a different pharmacological profile than that found in the parent drug. We have found unexpectedly that certain 9-substituted amino derivatives of tacrine act as prodrugs or depot agents and release tacrine in vivo over a prolonged period of time and are thus useful in the long-term treatment of patients with Alzheimer's disease.

SUMMARY OF THE INVENTION

Accordingly, the present invention is a compound of Formula I

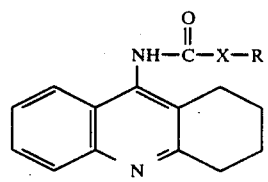

wherein

X is O or CH$_2$; and

R is alkyl of from one to twenty carbon atoms, or

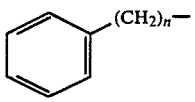

wherein n is zero or an integer of one to twenty; or a pharmaceutically acceptable acid addition salt thereof.

As prodrugs or depot derivatives of 1,2,3,4-tetra-hydro-9-acridinamine the Compounds of Formula I are useful as analgesic agents for the treatment of pain in mammals including man, as sleep aids and as agents for treating the symptoms of senile dementia, Alzheimer's disease, Huntington's chorea, tardive dyskinesia, hyperkinesia, mania or similar conditions of cerebral insufficiency characterized by decreased cerebral acetylcholine production or release.

A still further embodiment of the present invention is a pharmaceutical composition for administering an effective amount of a compound of Formula I in unit dosage form in the treatment methods mentioned above.

Finally, the present invention is directed to methods for production of a compound of Formula I.

DETAILED DESCRIPTION OF THE INVENTION

In the compounds of Formula I, the term "alkyl" means a straight or branched hydrocarbon radical having from one to twenty carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl, undecyl, dodecyl, tridecyl, tetradecyl, pentadecyl, hexadecyl, heptadecyl, octadecyl, nonadecyl, eicodecyl, and the like.

"Halogen" is fluorine, chlorine, bromine, or iodine.

For purposes of the present invention a "prodrug" refers to a compound of Formula 1 which is biotransformed gradually into 1,2,3,4-tetrahydro-9-acridinamine in a mammal.

For purposes of the present invention, a "depot derivative" refers to a compound of Formula I which is deposited in a body tissue or body cavity for a prolonged period of time, said compound serving as a reservoir which gradually releases 1,2,3,4-tetra-hydro-9-acridinamine at a controlled rate over an extended length of release time in a mammal.

Pharmaceutically acceptable acid addition salts of the compounds of Formula I include salts derived from nontoxic inorganic acids, such as hydrochloric, nitric, phosphoric, sulfuric, hydrobromic, hydriodic, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge, S. M., et al, "Pharmaceutical Salts," *Journal of Pharmaceutical Science,* Vol. 66, pages 1–19 (1977)).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free bases for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess asymmetric carbon atoms (optical centers); the racemates as well as the individual enantiomers are intended to be encompassed within the scope of the present invention.

A preferred compound of Formula 1 is one wherein R is alkyl of from one to twenty carbon atoms.

A more preferred compound of Formula 1 is one wherein R is alkyl of from four to fifteen carbon atoms.

Particularly valuable are:

N-(1,2,3,4-tetrahydro-9-acridinyl)decanamide; and

Octyl(1,2,3,4-tetrahydro-9-acridinyl)carbamate; or a pharmaceutically acceptable acid addition salt thereof.

The ability of a compound of Formula I to act as a prodrug or a depot agent and release tacrine in vivo over a prolonged period of time was demonstrated, for example, using the following assay procedure:

ASSAY PROCEDURE: A compound of Formula I was suspended in a 50:50 mixture of caster oil and benzyl benzoate at a concentration of 100 m9/ml. A single 300 mg/kg nonsterile dose of the selected compound of Formula I was administered intramusoularly into the left gluteal musole of three male Wistar rats. The depot dose was estimated to be approximately 30 times the single dose of tacrine given to rats when calculated on a molar basis. Blood samples were collected predose and 1, 3, 7, 11 and 14 days following drug administration. All blood samples were collected from the orbital sinus following ether anesthesia. Plasma was harvested and analyzed for tacrine.

The data in Table I shows the ability of representative compounds of Formula I to release tacrine in vivo over a prolonged period of time.

| | TACRINE PLASMA CONCENTRATION-TIME DATA FOLLOWING ADMINISTRATION OF A COMPOUND OF FORMULA I | | | | | | |
|---|---|---|---|---|---|---|---|
| Example Number | Compound | RAT | Tacrine Plasma Concentrations (ng/ml) | | | | |
| | | | Day 1 | Day 3 | Day 7 | Day 11 | Day 14 |
| 1 | N-(1,2,3,4-Tetrahydro-9-acridinyl)- | 1 | 1.66 | 0.00 | 3.51 | 3.59 | 1.48 |

TACRINE PLASMA CONCENTRATION-TIME DATA FOLLOWING ADMINISTRATION OF A COMPOUND OF FORMULA I

| Example Number | Compound | RAT | Tacrine Plasma Concentrations (ng/ml) | | | | |
|---|---|---|---|---|---|---|---|
| | | | Day 1 | Day 3 | Day 7 | Day 11 | Day 14 |
| | decanamide | 2 | 24.40 | 2.20 | 4.60 | 6.01 | 3.56 |
| | | 3 | 0.00 | 0.00 | a | 0.00 | 0.00 |
| | | Mean | 8.69 | 0.73 | 4.06 | 3.20 | 1.68 |
| 2 | Octyl (1,2,3,4-tetrahydro-9-acridinyl)- | 1 | 9.69 | 4.10 | 6.80 | 2.79 | 1.12 |
| | carbamate | 2 | 3.80 | 1.53 | 1.03 | 1.36 | 0.55 |
| | | 3 | 4.31 | 2.37 | 1.40 | 1.75 | 1.30 |
| | | Mean | 5.93 | 2.67 | 3.08 | 1.97 | 0.99 |

<sup>a</sup>Insufficient plasma for analysis

A compound of Formula I

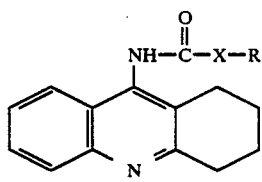   I wherein
X is O or $CH_2$; and
R is alkyl of from one to twenty carbon atoms, or

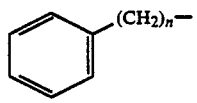

wherein n is zero or an integer of one to twenty; or a pharmaceutically acceptable acid addition salt thereof, may be prepared by reacting a compound of Formula II

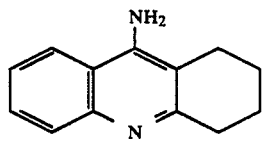   II with a compound of Formula III

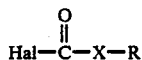   III wherein Hal is halogen, preferably chlorine or bromine, and X and R are as defined above in the presence of a base and solvent such as, for example, triethylamine and chloroform, n-butyllithium and tetrahydrofuran and the like at about 0° C. to about the reflux temperature of the solvent to afford a compound of Formula I.

Additionally, a compound of Formula $I_a$

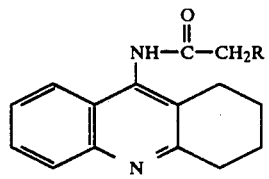   $I_a$ wherein R is as defined above may be prepared by reacting a compound of Formula II with a compound of Formula IV $HO_2C-CH_2R$   (IV)

wherein R is as defined above in the presence of a coupling reagent such as, for example, 1,3-dicyclohexylcarbodiimide (DCC), bis(2-oxo-3-oxazolidinyl)-phosphinic chloride (BOP-Cl) and the like, and if desired 1-hydroxybenzotriazole (HOBt) in the presence of a solvent such as, for example, methylene chloride, dimethylformamide, dioxane, tetrahydrofuran and the like at about −5° C. to about 25° C. to afford a compound of Formula $I_a$.

Other coupling methods that can be employed in preparing the compounds of Formula $I_a$ are discussed in "The Peptides. Analysis, Synthesis, Biology", Gross, E., and Meienhofer, J., eds, Academic Press, New York, New York, Volume 1, 1979.

Compounds of Formula III and Formula IV are either known or capable of being prepared by methods known in the art. The compound of Formula II is described in Petrow, V., *Journal of the Chemical Society*, pages 634 to 637 (1947).

The compounds of the present invention can be prepared and administered in a wide variety of oral and parenteral dosage forms. It will be obvious to those skilled in the art that the following dosage forms may comprise as the active component, either a compound of Formula I or a corresponding pharmaceutically acceptable salt of a compound of Formula I.

Preferably the compounds of the present invention are administered orally, intramuscularly or subcutaneously.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymelhylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 7,000 mg according to the particular application and the potency of the active component. The composition can, if desired, also contain other compatible therapeutic agents.

In therapeutic use as prodrugs or depot derivatives of 1,2,3,4-tetrahydro-9-acridinamine the compounds utilized in the pharmaceutical method of this invention are administered at the initial dosage of about 0.01 mg to about 100 mg per kilo9ram daily. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventors' preferred methods for preparing the compounds of the invention.

EXAMPLE 1

N-(1,2,3,4-Tetrahydro-9-acridinyl)decanamide

Freshly distilled decanoyl chloride, 5.18 g (0.029 mol), is slowly added to a mixture of 2.94 g (0.029 mol) of triethylamine and 5.82 g (0.029 mol) of 1,2,3,4-tetrahydro-9-acridinamine (Petrow, V., Journal of the Chemical Society, pages 634 to 637 (1947)) in 150 ml of Chloroform. The mixture is heated at reflux for two hours, cooled to room temperature, filtered, and the filtrate evaporated to afford, after repeated washing with diethyl ether, 1.67 g of N-(1,3,4,5-tetrahydro-9-acridinyl)decanamide as a yellow solid: mp 123–126° C.

EXAMPLE 2

Octyl (1,2,4,4-tetrahydro-9-acridinyl)carbamate n Butyllithium, 0.033 mol, is added to a suspension of 6.5g (0.033 mol) of 1,2,3,4-tetra -hydro-9-acridinamine (Petrow, V., Journal of the Chemical Society, pages 634 to 637 (1947)) in 200 ml of tetrahydrofuran at 0° C. The mixture is stirred at 0° C. for 20 minutes, the cooling bath removed and 6.36 g (0.033 mol) of octyl chloroformate added and the solution stirred over the weekend. Water, 200 ml, is added and the mixture extracted with ethyl acetate. The ethyl acetate layer is separated and evaporated to afford a yellow oil. Chromatography (elution with isopropanol-chloroform (5:95)) affords 6.59 g of octyl (1,2,3,4-tetrahydro-9-acridinyl)carbamate, as a yellow solid; mp 96–99° C.

We claim:

1. A compound of Formula I

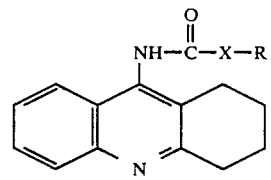

wherein

X is O or $CH_2$; and

R is alkyl of from one to twenty carbon atoms, or

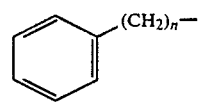

wherein n is zero or an integer of one to twenty with the exclusion of the compound of Formula

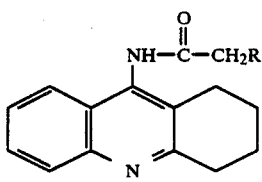

wherein R is alkyl of from one to four or

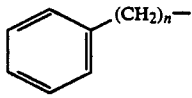

wherein n is 0 or an integer of one to two; or a pharmaceutically acceptable acid addition salt thereof.

2. A compound according to claim 1, in which R is alkyl of from one to twenty carbon atoms with the exclusion of the compound of Formula

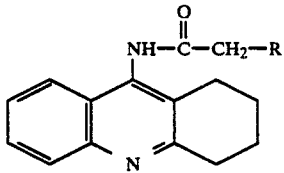

wherein R is alkyl of from one to four.

3. A compound according to claim 2, in which R is alkyl of from four to fifteen carbon atoms with the exclusion of the compound of Formula

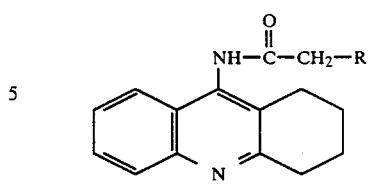

wherein R is alkyl of four carbon atoms.

4. A compound according to claim 3, and being N-(1,2,3,4-tetrahydro-9-acridinyl)decanamide.

5. A compound according to claim 3, and being octyl (1,2,3,4-tetrahydro-9-acridinyl)carbamate.

6. A method of treating the symptoms of cognitive decline in an elderly patient comprising a cholinergically effective amount of a compound according to claim 1 in unit dosage form.

7. A method of treating the symptoms of Alzheimer's disease in a patient comprising a cholinergically effective amount of a compound according to claim 1 in unit dosage form.

8. A pharmaceutical composition for the treatment of the symptoms of cognitive decline in an elderly patient comprising a cholinergically effective amount of a compound according to claim 6 in combination with a pharmaceutically acceptable carrier.

9. A pharmaceutical composition for the treatment of the symptoms of Alzheimer's disease in a patient comprising a cholinergically effective amount of a compound according to claim 7 in combination with a pharmaceutically acceptable carrier.

10. A pharmaceutical composition as claimed in claim 9 suitable for oral administration.

11. A pharmaceutical composition as claimed in claim 9 suitable for parenteral administration.

12. A pharmaceutical composition as claimed in claim 11 suitable for intramusoular and subcutaneous administration.

* * * * *

UNITED STATES PATENT AND TRADEMARK OFFICE
CERTIFICATE OF CORRECTION

PATENT NO. : 4,999,430
DATED : Mar. 12, 1991
INVENTOR(S) : Jeffrey A. Kester, etal It is certified that error appears in the above-indentified patent and that said Letters Patent is hereby corrected as shown below:

On title page, item [54] and col. 1, line 2, "ACRISINAMINE" should read --ACRIDINAMINE--

Signed and Sealed this

Twenty-fourth Day of May, 1994

Attest:

BRUCE LEHMAN

*Attesting Officer*      *Commissioner of Patents and Trademarks*